(12) United States Patent
Ouwerkerk

(10) Patent No.: US 10,694,969 B2
(45) Date of Patent: Jun. 30, 2020

(54) DRY SKIN CONDUCTANCE ELECTRODE

(71) Applicant: KONINKLIJKE PHILIPS N.V., Eindhoven (NL)

(72) Inventor: Martin Ouwerkerk, Culemborg (NL)

(73) Assignee: Koninklijke Philips N.V., Eindhoven (NL)

( * ) Notice: Subject to any disclaimer, the term of this patent is extended or adjusted under 35 U.S.C. 154(b) by 548 days.

(21) Appl. No.: 15/644,894

(22) Filed: Jul. 10, 2017

(65) Prior Publication Data
US 2017/0303812 A1    Oct. 26, 2017

Related U.S. Application Data

(62) Division of application No. 14/002,503, filed as application No. PCT/IB2012/050528 on Feb. 6, 2012, now abandoned.

(30) Foreign Application Priority Data

Mar. 2, 2011    (EP) .................................... 11156641

(51) Int. Cl.
*A61B 5/053*    (2006.01)
*A61B 5/00*    (2006.01)

(52) U.S. Cl.
CPC ............ *A61B 5/053* (2013.01); *A61B 5/0533* (2013.01); *A61B 5/681* (2013.01); *A61B 2562/125* (2013.01)

(58) Field of Classification Search
CPC .. A61B 5/053; A61B 5/0531; A61B 2562/125
See application file for complete search history.

(56) References Cited

U.S. PATENT DOCUMENTS 3,681,136 A * 8/1972 Leonard ............... A61B 5/0408
427/126.1
4,235,241 A * 11/1980 Tabuchi ............... A61B 5/0408
600/396

(Continued)

FOREIGN PATENT DOCUMENTS

CN    101322645 A    12/2008
CN    101848669 A    9/2010

(Continued)

OTHER PUBLICATIONS

Hoffman et al. Long-Term Characterization of Electrode Materials for Surface Electordes in Biopotential Recording.2006 International Conference of the IEEE Engineering in Medicine and Biology Society. (Year: 2006).*

Dias et al. New dry electrodes based on iridium oxide for non-invasive bio potential recordings and stimulation. Sensors and Actuators A: Physical. vol. 164 Issues 1-2. 2010/ pp. 28-34 (Year: 2010).*

(Continued)

*Primary Examiner* — Cachet I Proctor

(57) ABSTRACT

The present invention relates to a dry skin conductance electrode for contacting the skin of a user. In order to provide a dry skin conductance electrode for long-term measurements which does not cause problems to the user while still providing a good signal level, the electrode comprises a material made of a noble metal doped with at least one dopant selected from the group consisting of hydrogen, lithium, sodium, potassium, rubidium, caesium and beryllium. The present invention also relates to a skin conductance sensor, a wristband and an emotional event detection system.

12 Claims, 9 Drawing Sheets

(56) References Cited

U.S. PATENT DOCUMENTS

| | | | |
|---|---|---|---|
| 5,003,978 A * | 4/1991 | Dunseath, Jr. | A61B 5/0408 600/391 |
| 5,415,176 A | 5/1995 | Sato et al. | |
| 6,370,425 B1 | 4/2002 | Oguma | |
| 7,052,472 B1 | 5/2006 | Miller et al. | |
| 8,406,841 B2 * | 3/2013 | Lin | A61B 5/0408 600/372 |
| 9,101,734 B2 | 8/2015 | Selker | |
| 2002/0019586 A1 * | 2/2002 | Teller | A61B 5/02055 600/300 |
| 2002/0068887 A1 * | 6/2002 | Kikumoto | A61H 7/007 601/49 |
| 2004/0158166 A1 * | 8/2004 | Levengood | A61B 5/04 600/547 |
| 2004/0181141 A1 | 9/2004 | Kislov et al. | |
| 2005/0010161 A1 | 1/2005 | Sun et al. | |
| 2005/0101853 A1 | 5/2005 | Rowe et al. | |
| 2008/0091089 A1 * | 4/2008 | Guillory | A61B 5/0478 600/301 |
| 2008/0208024 A1 | 8/2008 | Hagino et al. | |
| 2008/0262376 A1 | 10/2008 | Price | |
| 2009/0069740 A1 | 3/2009 | Visco et al. | |
| 2009/0281475 A1 | 11/2009 | Nisato et al. | |
| 2010/0049079 A1 | 2/2010 | Davies | |
| 2010/0063478 A1 | 3/2010 | Selkee | |
| 2010/0268056 A1 | 10/2010 | Picard et al. | |
| 2011/0028803 A1 | 2/2011 | Ollmar | |
| 2011/0118655 A1 * | 5/2011 | Fassih | A61N 1/205 604/20 |
| 2013/0338470 A1 | 12/2013 | Ouwerkerk | |

FOREIGN PATENT DOCUMENTS

| | | |
|---|---|---|
| DE | 102008013731 | 9/2009 |
| EP | 2179240 A1 | 4/2010 |
| JP | 4158835 A | 6/1992 |
| JP | H07222806 A | 8/1995 |
| JP | 2009174948 A | 8/2009 |

OTHER PUBLICATIONS

Dias et al: "New Dry Electrodes Based on Iridium Oxide (IRO) for Non-Invasive Biopotential Recordings and Stimulation", Sensors and Actuators A 164(2010), 28-34.

Fonseca et al: "A Novel Dry Active Electrode for EEG Recording", IEEE Trans. on Biomed. Eng. Jan. 2007, vol. 54, Issue 1.

Pandian: "Wireless Sensor Network for Wearable Physiological Monitoring"; Journal of Networks, vol. 3, No. 5, May 2008, pp. 21-29.

Poh: "A Wearable Sensor for Unobstructive, Long-Term Assessment of Electrodermal Activity", IEEE Transactions on Biomedical Engineering, vol. 57, No. 5, May 2010, pp. 1243-1252.

Yoo, J. et al., "A 5.2mW Self-Configured Wearable Body Sensor Network Controller and a 12 u W Wirelessly Powered Sensor for a Continuous Health Monitoring System", IEEE Journal of Solid-State Circuits, 2010:45(1), pp. 178-188.

Oosaka, T., "Electrochemical Method", Japanese literature, Apr. 20, 1990.

Matsuo, M., "Electrical properties of Biomedical Metal Electrodes", Apr. 1970.

Yamaguchi, H., "Important factors of the bioelectrodes", Research Institute of Applied Electricity, Hokkaido University, 1984.

* cited by examiner

DRY SKIN CONDUCTANCE ELECTRODE

CROSS-REFERENCE TO RELATED APPLICATIONS

The present application is a divisional of U.S. application Ser. No. 14/002,503, filed Aug. 30, 2013, which is the U.S. National Phase application under 35 U.S.C. § 371 of International Application No. PCT/IB2012/050528, filed Feb. 6, 2012, which claims the benefit of European Application No. 11156641.0, filed Mar. 2, 2011. These applications are hereby icorporated by reference herein.

FIELD OF THE INVENTION

The present invention relates to a dry skin conductance electrode for contacting the skin of a user and to a skin conductance sensor comprising at least two dry electrodes, wherein the sensor is adapted to sense a user's skin conductance between the at least two dry electrodes. The present invention also relates to a wristband comprising such a skin conductance sensor and an emotional event detection system comprising such a skin conductance sensor.

BACKGROUND OF THE INVENTION

It is known that skin conductance of a user is related with the level of arousal of a user. Everything that emotionally touches the user activates the sweat glands in the skin leading to a better conductor path through the skin. For example, in a known lie detector or polygraph, a skin conductance sensor connected to the palm of the hand or to the fingers is used.

Commonly, gel electrodes are used for skin conductance sensors. These gel electrodes offer a high signal level. However, prolonged wearing of gel electrodes causes undesirable side effects, such as a white swelling of the skin caused by hydration.

When the period of measurement is long, the skin conductance sensor needs to be comfortable for the user. In the article "A Wearable Sensor for Unobtrusive, Long-Term Assessment of Electrodermal Activity", *Ming-Zher Poh, Nicholas C. Swenson, and Rosalind W. Picard, IEEE Transactions on Biomedical Engineering*, Vol. 57, No. 5 (2010) 1243-1252, a wrist-worn integrated sensor is disclosed. This sensor has Ag/AgCl electrodes, and no conductive gel applied to the electrodes. However, due to the Ag/AgCl material, prolonged wearing of this device causes brown skin coloration due to the injection of silver ions into the skin, which is an undesirable side effect.

SUMMARY OF THE INVENTION

It is an object of the present invention to provide, for long-term measurements, a dry skin conductance electrode, as well as a skin conductance sensor, wristband and emotional event detection system comprising such dry electrodes, which does not cause problems to the user, such as skin irritation or skin coloration, while still providing a good signal level.

In a first aspect of the present invention, a dry skin conductance electrode for contacting the skin of a user is presented, the electrode comprising a material made of a noble metal doped with at least one dopant selected from the group consisting of hydrogen, lithium, sodium, potassium, rubidium, caesium and beryllium.

In a second aspect of the present invention, a skin conductance sensor comprising at least two dry electrodes is presented, that is adapted to sense a user's skin conductance between the at least two dry electrodes, wherein at least one of the electrodes is the dry skin conductance electrode as described above.

In a further aspect of the present invention a wristband is presented that comprises such a skin conductance sensor.

In a still further aspect of the present invention an emotional event detection system for detecting an emotional event of a user is presented, that comprises such a skin conductance sensor, a transmission link for transmitting data indicative of the sensed skin conductance, and a processing unit adapted to process the transmitted data and detect an emotional event in the user based on the transmitted data.

The present invention is based on the idea to provide a skin conductance sensor for long-term measurements (for example several hours or days) comprising dry electrodes with a good non-polarizable electronic skin-electrode interface. A dry skin conductance electrode is an electrode which does not require the use of a conductance gel for skin conductance measurements, thus also called gel-free skin conductance electrode. The dry, gel-free skin conductance electrode makes direct contact with the skin of the user, thus forming a skin-electrode interface. The skin-electrode interface is an interface between a medium where the current carriers are predominantly electronic (electrode), and a medium where the current carriers are predominantly ionic (skin). Usually, such an interface suffers from a poor charge transfer, leading to the formation of a space charge. A non-polarizable skin-electrode interface is provided when there is charge transfer at the interface. A perfectly non-polarizable interface would exhibit no impedance to the charge transfer, which is however not possible in practice. At a non-polarizable skin-electrode interface, due to an electrochemical reaction, ions are injected into the skin from the positive electrode. Thus, electrons are left in the positive electrode, causing a current flow to take place. At the negative electrode, ions are absorbed from the skin, in particular protons, sodium ions or potassium ions, as the fluid secreted by sweat glands contains mainly hydrogen, sodium and potassium. The ions are incorporated into the metal matrix of the negative electrode material as atoms, after the acceptance of an electron.

Since the dry skin conductance electrode comprises a noble metal doped with at least one dopant selected from the group consisting of hydrogen, lithium, sodium, potassium, rubidium, caesium and beryllium, the charge transfer process (ionic exchange between the skin and the electrode material) and thus the interface is improved, leading to a good non-polarizable interface. No gel is needed and no skin problems are caused, such as skin coloration due to the injection of silver ions to the skin.

A dopant is generally a trace impurity element that is inserted into a base material in very low concentrations, for example in order to alter a specific property of the base material. In the claimed material, a noble metal is used as base material, since these metals are most likely not to take part in the electrochemical reaction with the skin. In general, noble metals are the group of ruthenium (Ru), rhodium (Rh), palladium (Pd), silver (Ag), osmium (Os), iridium (Ir), platinum (Pt), and gold (Au). The noble metal of the claimed material should not cause dermatological problems to the user. In general, the claimed material should be non-toxic, or at a toxic level which is below a value that is harming to the user. For example, even though beryllium (Be) is toxic, it can be used as the dopant, if the concentration of the dopant is below a value that is harming to the user.

Preferred embodiments of the invention are defined in the dependent claims. It shall be understood that the claimed skin conductance sensor, wristband or emotional detection system has similar and/or identical preferred embodiments as the claimed skin conductance electrode and as defined in the dependent claims.

According to a first embodiment, the noble metal is at least one element selected from the group of gold, palladium and platinum. These noble metals are especially suitable in combination with the dopants mentioned above.

Further, in a second embodiment, the dopant is lithium, sodium or potassium. These dopants are especially suitable when used in noble metals. In particular, the atoms of these dopants have a relatively high mobility due to their relatively low atomic radius.

Any combination of the above mentioned elements of the first embodiment and the elements of the second embodiment is possible. In one embodiment, the dopant is an element from the first group of the periodic table or monovalent. Further, in an embodiment, the dopant is an alkali metal. Alkali metals are generally the group of lithium (Li), sodium (Na), potassium (K), rubidium (Rb), caesium (Cs), and francium (Fr).

In a preferred embodiment, the material is made of gold, palladium or platinum and the dopant is lithium, therefore: gold doped with lithium, palladium doped with lithium or platinum doped with lithium. Since the lithium atoms have a low atomic radius and thus a high mobility, diffusion processes are minimized.

In another preferred embodiment, the material is made of gold and the dopant is lithium, sodium or potassium. In a further embodiment, the difference in ionization potential between the noble metal and the dopant is at or above a level at which the noble metal is prevented from taking part in the electrochemical reaction with the skin. Thus, it is prevented that ions of the noble metals are also injected into the skin due to electrochemical reaction.

According to a further embodiment, the concentration of the dopant is between 0.1 and 5%, in particular between 0.5 and 3%, in particular between 0.7 and 1.3%, in particular about 1%±0.2%. It is achieved that the concentration of the dopant is sufficiently high to prevent depletion and sufficiently low not to change the main properties of the noble metal.

In a still further embodiment, the material is located at an outer surface of the electrode for interfacing the skin. This enables that the claimed material is in direct contact with the skin.

In another embodiment, the electrode comprises an outer layer which is formed of the material. Thus, only a thin outer layer of the claimed material is needed which reduces costs, as the remaining part of the electrode can be made of a cheaper material.

In a variant of the embodiment above, the electrode further comprises an inner layer beneath the outer layer. This can provide more stability to the electrode and can reduce manufacturing costs.

In particular, in this variant, the inner layer is formed of nickel and/or brass. This reduces manufacturing costs, as these materials are generally cheaper than noble metals.

In an embodiment of the skin conductance sensor, the skin conductance sensor comprises a voltage generator for applying a voltage between the at least two dry electrodes, a measuring means for measuring a current between the at least two dry electrodes, and a calculating unit for calculating skin conductance based on the measured current. This provides for a skin conductance sensor that is easy to implement. Preferably, the applied voltage is a constant voltage.

In an embodiment of the skin conductance sensor, the two dry electrodes comprise the same material, in particular the claimed material. In an alternative embodiment of the skin conductance sensor, the two dry electrodes comprise different materials. In one embodiment, the positive electrode comprises the claimed material. Alternatively or cumulatively, the negative electrode comprises the claimed material.

In an embodiment of the wristband or the skin conductance sensor, the at least two dry electrodes are arranged for contacting the volar side of the wrist of the user. Hence, good measurement can be obtained, since the volar side of the wrist is a region in which the skin conductance is at the same level. Also there is generally no hair, which could influence the measurement, in this region.

In an embodiment of the emotional event detection system or the skin conductance sensor, the transmission link is a wireless link between the skin conductance sensor and the processing unit. This enables to provide for a comfortable mobile system.

In an embodiment of the emotional event detection system, the processing unit is adapted to detect a peak having a particular rising slope and/or a particular down slope in the transmitted skin conductance data. Skin conductance is related with the level of arousal of the user. Hence, an easy way of determining emotional events from skin conductance data is provided.

In a still further embodiment of the emotional detection system, the system comprise at least one further sensor, such as a heart rate sensor, for example for measuring heart rate variations, a breathing sensor, a blood sensor, a body temperature sensor, a voice sensor, a camera for capturing the face of the user, or the like. This enables to combine measurements from the skin conductance sensor with measurements of other sensors. Thus, accuracy of the emotional event detection is improved.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
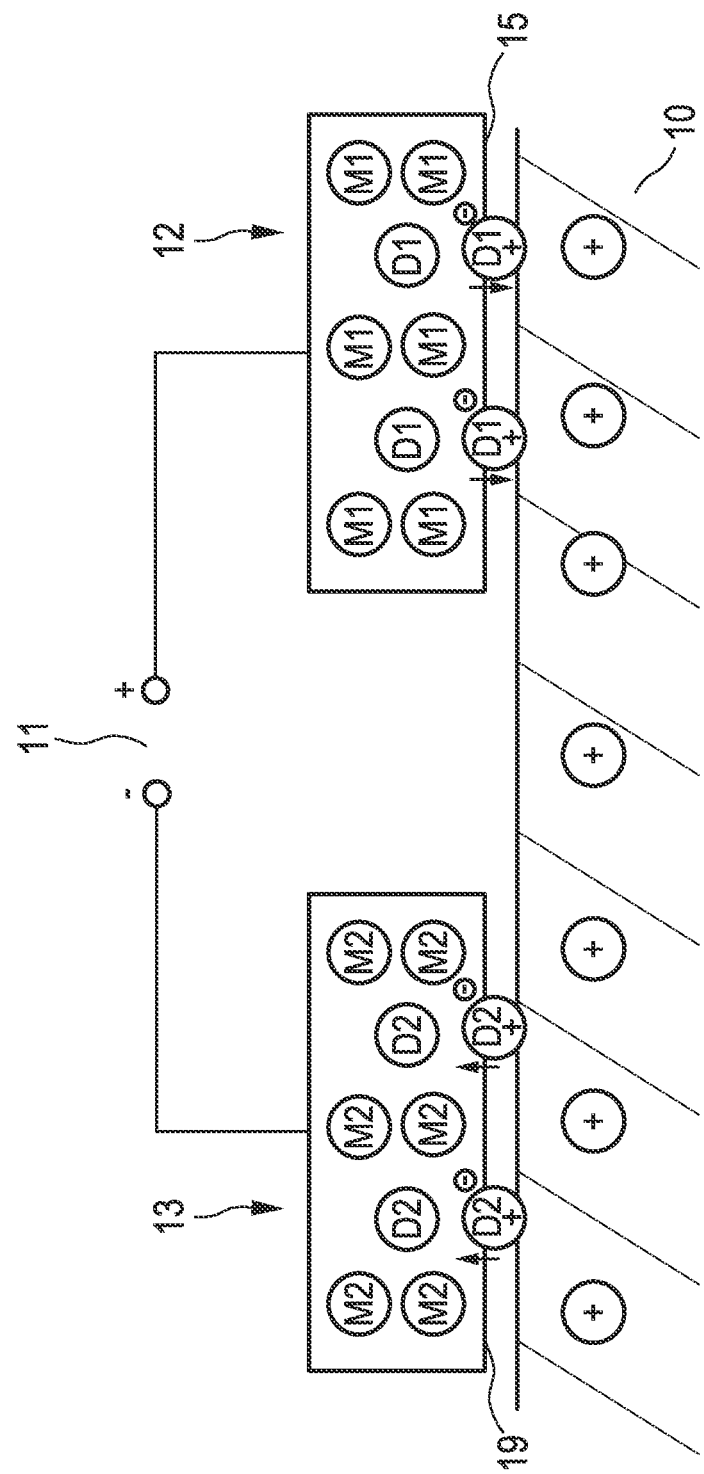
FIG. 1 shows an interface between skin and two dry electrodes according to an embodiment of the present invention.

FIG. 1 shows an interface between skin 10 of a user and two dry electrodes 12, 13 according to an embodiment of the present invention. For example, when the user wears a skin conductance sensor 20 comprising the two dry electrodes 12, 13, the two dry electrodes 12, 13 are placed on the skin of the user. A voltage 11 is applied between the two dry electrodes 12, 13 such that a positive electrode 12 and a negative electrode 13 is provided. The positive electrode 12 has an outer surface 15 which interfaces with the skin 10 and the negative electrode 13 has an outer surface 19 which interfaces with the skin 10. The skin-electrode interface is an interface between a medium where the current carriers are predominantly electronic (electrodes 12, 13 in FIG. 1), and a medium where the current carriers are predominantly ionic (skin 10 in FIG. 1). Usually such an interface suffers from a poor charge transfer, leading to the formation of a space charge.

However, as can be seen in FIG. 1, a non-polarizable skin-electrode interface is provided as there is charge transfer at the interface. The dry skin conductance electrodes 12, 13 each comprise a material made of a noble metal, marked with M, doped with at least one dopant, marked with D1, selected from the group consisting of hydrogen, lithium, sodium, potassium, rubidium, caesium and beryllium. Due to an electrochemical reaction, ions of the dopant, marked with D1+, are injected into the skin 10 from the material of the positive electrode 12. Thus, electrons are left in the positive electrode, causing a current flow to take place. At the negative electrode 13, ions, marked with D2+, are absorbed from the skin.

These ions D2+ are in particular hydrogen, sodium or potassium, as the fluid secreted by sweat glands contains mainly hydrogen, sodium and potassium. The ions D2+ are incorporated into the metal matrix of the material of the negative electrode 13 as atoms D2, after the acceptance of an electron. Therefore, the charge transfer process and thus the interface is improved, leading to a good non-polarizable interface. The ionic exchange between the skin 10 and the material of the electrode 12, 13 is facilitated.

In the embodiment of FIG. 1, the two dry electrodes 12, 13 of the skin conductance sensor comprise different materials at their outer surfaces 15, 19. Positive electrode 12 comprises a material made of a noble metal M1 doped with a dopant D1 and negative electrode 13 comprises a material made of a noble metal M2 doped with a dopant D2. In an alternative embodiment, the two dry electrodes 12, 13 can comprise the same material. For example, when the material is made of palladium doped with lithium (Pt—Li), this material can be used for both electrodes, the positive electrode 12 and the negative electrode 13, as it is optimal for both electrodes.

In a first embodiment, the noble metal is gold, palladium or platinum, or any combination, thus any alloy. In a second embodiment, the dopant is lithium, sodium or potassium. In another embodiment the dopant is an element from the first group of the periodic table or monovalent, in particular an alkali metal, thus from the group of lithium (Li), sodium (Na), potassium (K), rubidium (Rb), caesium (Cs), and francium (Fr). In another embodiment, also beryllium (Be), even though toxic, can be used as the dopant, if the concentration of the dopant is below a value that is harming to the user.

In a preferred embodiment, the material is made of gold doped with lithium (Au—Li), palladium doped with lithium (Pd—Li) or platinum doped with lithium (Pt—Li). In another preferred embodiment, the material is made of gold and the dopant is lithium, sodium or potassium, therefore: gold doped with lithium (Au—Li), gold doped with sodium (Au—Na) or gold doped with potassium (Au—K). In a most preferred embodiment, the material is made of gold doped with lithium (Au—Li, for example with a dopant concentration between 0.1 and 5%, in particular between 0.5 and 3%, in particular between 0.7 and 1.3%, in particular 1%±0.2%. In this case for example, the difference in ionization potential between the noble metal and the dopant is at or above a level at which the noble metal is prevented from taking part in the electrochemical reaction with the skin 10. Thus, it is prevented that ions of the noble metal are also injected into the skin 10 due to electrochemical reaction.

Figure 2:
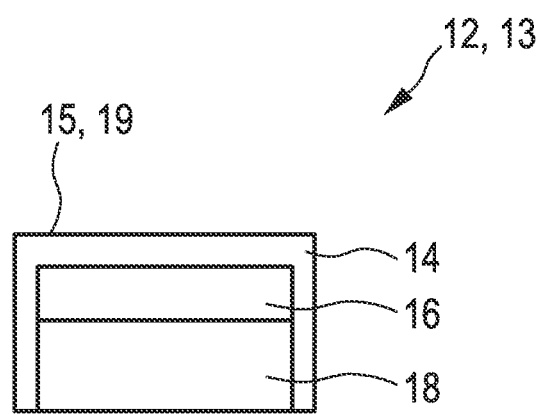
FIG. 2 shows a cross section of a skin conductance electrode according to an embodiment of the present invention.

FIG. 2 shows a cross-section of a skin conductance electrode 12, 13 according to an embodiment. The electrode 12, 13 has an outer surface 15, 19 for interfacing with the skin 10. The material described above is located at the outer surface 15, 19. In FIG. 2, the electrode 12, 13 comprises an outer layer 14 which is formed of the material. The outer layer 14 comprises the outer surface 15 for interfacing with the skin 10. The electrode 12, 13 further comprises a first inner layer 16 located beneath the outer layer 14. The electrode 12, 13 further comprises a second inner layer, or base layer, 18 located beneath the first inner layer 16.

In the most preferred embodiment, the second inner layer, or base layer, 18, is formed of brass, the first inner layer 16 is a formed of nickel, and the outer layer 14 is formed of a material made of gold doped with monovalent lithium ions (Au—Li)

In an exemplary manufacturing method, the material of the second inner layer 18, such as brass in the most preferred embodiment, for example in the form of a plate, is polished and electrochemically plated with the first inner layer 16, such as nickel in the most preferred embodiment. Then, the outer layer 14, such as gold doped with lithium in the most preferred embodiment, is applied by sputtering. Optionally, before sputtering the outer layer 14, the material can be melted, such as in a closed quartz vessel, then cooled, afterwards flattened and the sputter targets, for example of round form, can be cut out. Also optionally, before sputtering the outer layer 14, the surface of the first inner layer 16 can be cleaned using reactive ion etching in order to improve the bonding between the first inner layer 16 and the outer layer 14. An alternative to applying the outer layer 14 by sputtering is the co-deposition in vacuum by evaporation and/or e-beam deposition. For example, gold can be e-beam deposited and lithium can be deposited in vacuum by evaporation from a heated crucible, due to the low melting point of lithium. Optionally, the thickness of the layer can be monitored so that the deposition speed can be controlled. A good stability of the outer layer 14 can thus be realized throughout the layer. The thickness of the outer layer 14 can for example be in the order of microns, in particular less than 1 micron.

Figure 3:
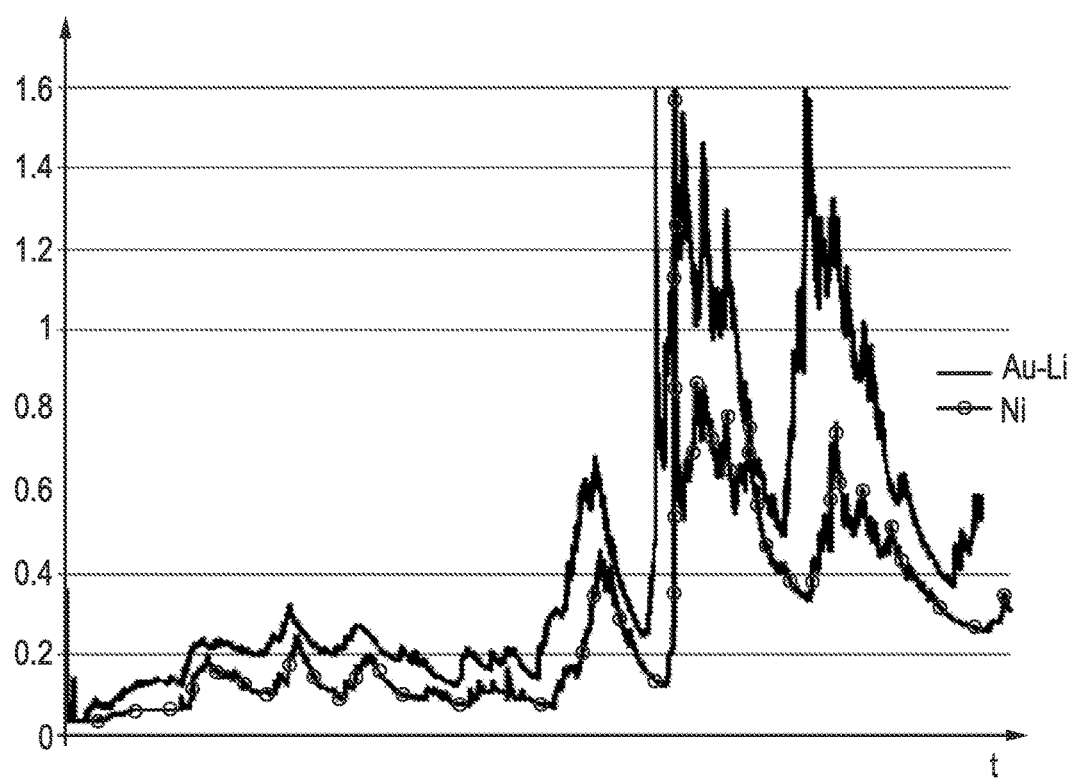
FIG. 3 shows a first skin conductance trace, sensed by a skin conductance sensor according to an embodiment of the present invention, and a second skin conductance trace for comparison.

FIG. 3 shows skin conductance traces. The measured skin conductance values over time form a skin conductance trace. The x-axis is the time axis, for example measured in minutes (min), and the y-axis is the skin conductance axis, for example measured in microSiemens (µS). Skin conductance, or also called galvanic skin response (GSR), is a measure of the electrical conductance of the skin, which varies with its moisture level, thus the sweat gland activity.

Figure 3A:
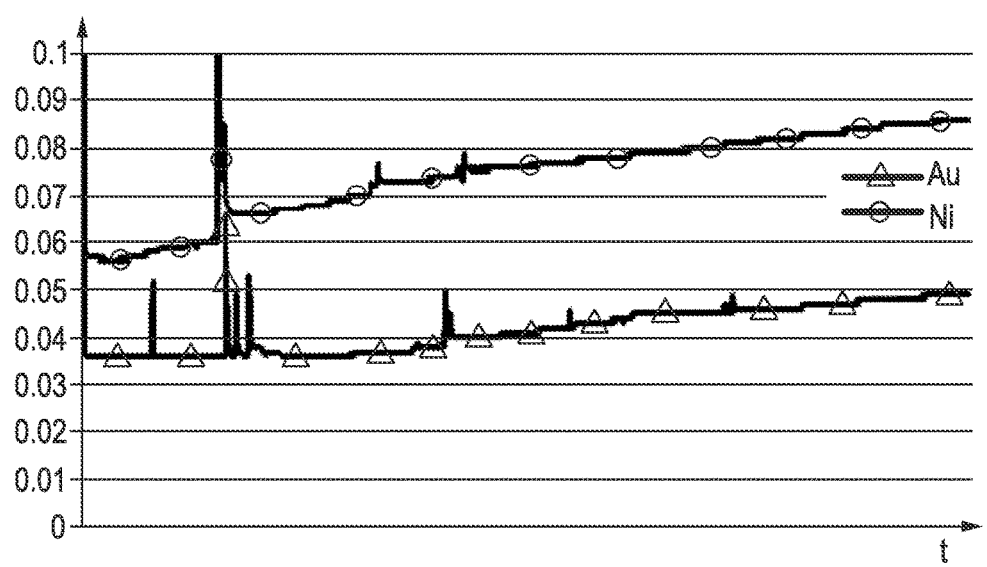
FIG. 3a shows two skin conductance traces for comparison.

In particular, FIG. 3 shows a first skin conductance trace, sensed by a skin conductance sensor according to an embodiment, namely the most preferred embodiment described above, using a material made of gold doped with lithium at the outer surface of the electrode. This first skin conductance trace is illustrated by a plain solid line. For comparison, FIG. 3 also shows a second skin conductance trace, illustrated by the circled solid line, in which a conventional electrode having nickel at the outer surface has been used. The improved signal level of the first skin conductance trace (Au—Li) compared to the second skin conductance trace (Ni) can be clearly seen in FIG. 3. If an undoped gold material (Au) at the outer surface of the electrode material would be used, the signal level of the corresponding skin conductance trace (not shown in FIG. 3) would be even lower than with the nickel (Ni) electrode. For mere comparison purposes, this is illustrated in FIG. 3a showing a skin conductance trace sensed by a skin conductance sensor having a conventional nickel (Ni) electrode and a skin conductance trace sensed by a skin conductance sensor having a gold (Au) electrode.

Figure 3B:
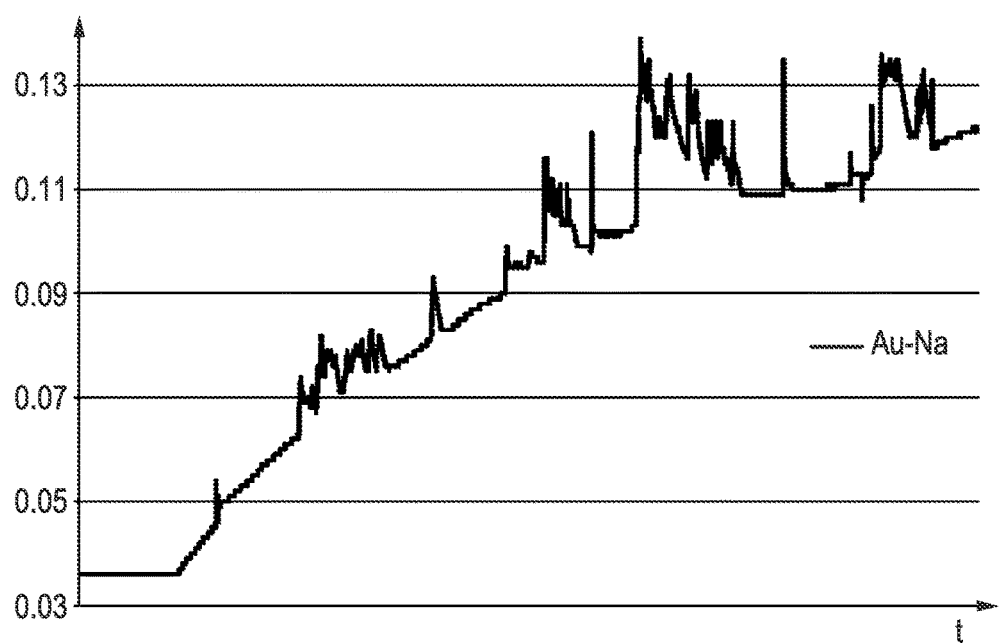
FIG. 3b shows a skin conductance trace, sensed by a skin conductance sensor according to an embodiment of the present invention.

By using an electrode comprising a material made of gold doped with potassium (Au—K) or gold doped with sodium (Au—Na), similar results as with a material made of gold doped with lithium (Au—Li) can be obtained. However, with potassium and sodium, there is a large period of signal increase, compared to the use of lithium, after first use due to diffusion processes. More time is needed for the skin conductance to reach a stable level, compared to the Au—Li example shown in FIG. 3. This is exemplary illustrated in FIG. 3b, showing a skin conductance trace, sensed by a skin conductance sensor comprising an electrode comprising gold doped with sodium (Au—Na). The slow increase of the signal can be seen in FIG. 3b. This can be explained with the difference in radius between sodium, potassium and lithium: potassium radius: 138 µm, sodium radius: 102 µm, lithium radius: 76 µm. The smaller the ion is, the easier it is to penetrate the skin due to its increased mobility.

Similar results as shown for gold doped with lithium, potassium or sodium can also be obtained by doping platinum with lithium, potassium or sodium.

Figure 4:
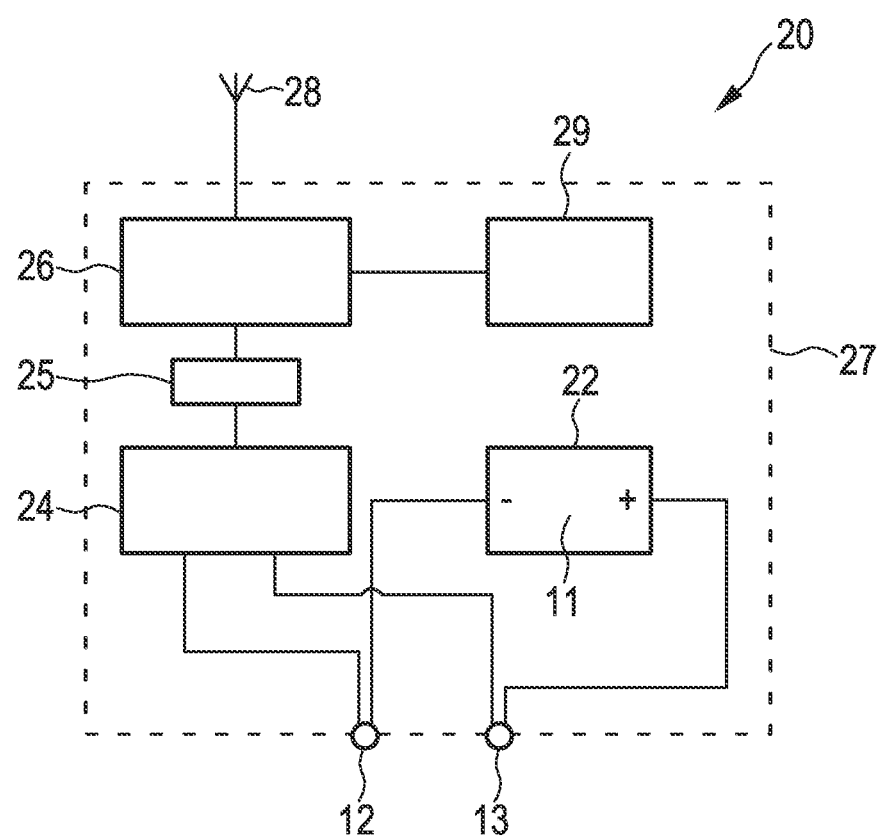
FIG. 4 shows a schematic block diagram of a skin conductance sensor according to an embodiment of the present invention.

FIG. 4 shows a schematic block diagram of a skin conductance sensor 20 according to an embodiment. The skin conductance sensor 20 comprises two dry electrodes 12, 13. The skin conductance sensor 20 further comprises a voltage generator 22 for applying a voltage 11, in particular a constant voltage, between the two electrodes 12, 13. Normally, a small voltage is applied, for example less than 1.2 V. Such a small voltage induces a small current, for example in the order of 1 µA, through the skin. The skin conductance sensor 20 further comprises a measuring unit 24 for measuring a current or voltage drop between the two dry electrodes 12, 13. An A/D converter 25 of the skin conductance sensor 20 digitizes the measured current or voltage drop. The skin conductance sensor further comprises a calculating unit 26, such as a processor, for calculating a skin conductance based on the measured current or voltage drop. It should be understood, that also the skin resistance can be calculated which is the inverse of the skin conductance.

The measured skin conductance values, or the skin conductance trace, can for example be transmitted by a transmitter 28 over a wireless transmission link. Additionally or alternatively, these measured skin conductance values can be stored in a memory unit 29.

The skin conductance sensor 20 comprises a casing 27. All or only some of the components described above can be integrated in the casing 27. However, some components may also be separate parts. In particular, the electrodes 12, 13 can be separate parts.

Figure 5:
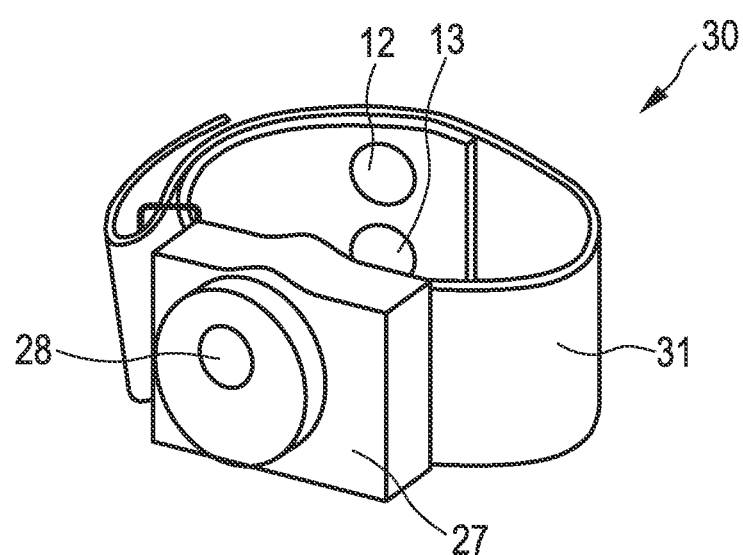
FIG. 5 shows an illustration of a wristband according to an embodiment of the present invention.

FIG. 5 shows an illustration of a wristband according to an embodiment. The wristband 30 comprises a skin conductance sensor 20 as described above, in particular as illustrated in FIG. 4. The wristband 30 comprises a wristband material part 31, for example made of a textile or plastic, which loops around the wrist of the user. Even though called wristband, the wristband 30 could also be worn around the ankle or other suitable body part. The two dry electrodes 12, 13 are integrated into the wristband 30, in particular integrated into the wristband material part 31. The two dry electrodes 12, 13 are arranged such that they contact the volar side of the wrist when the wristband 30 is worn by the user. The electrodes 12, 13 have a round form in FIG. 5, however any other suitable electrode form may be used. In particular, the electrodes 12, 13 in FIG. 5 are in the form of clothing buttons. A casing 27 comprises a voltage generator 22, a measuring unit 24, and a calculating unit 26. The two electrodes 12, 13 are separate parts and are connected to the casing 27 by means of wires located within the wristband. Alternatively, the two electrodes 12, 13 can also be integrated into the casing 27. In FIG. 5, a transmitter 28 for wirelessly transmitting the measured skin conductance values is integrated into the casing 27.

Figure 6:
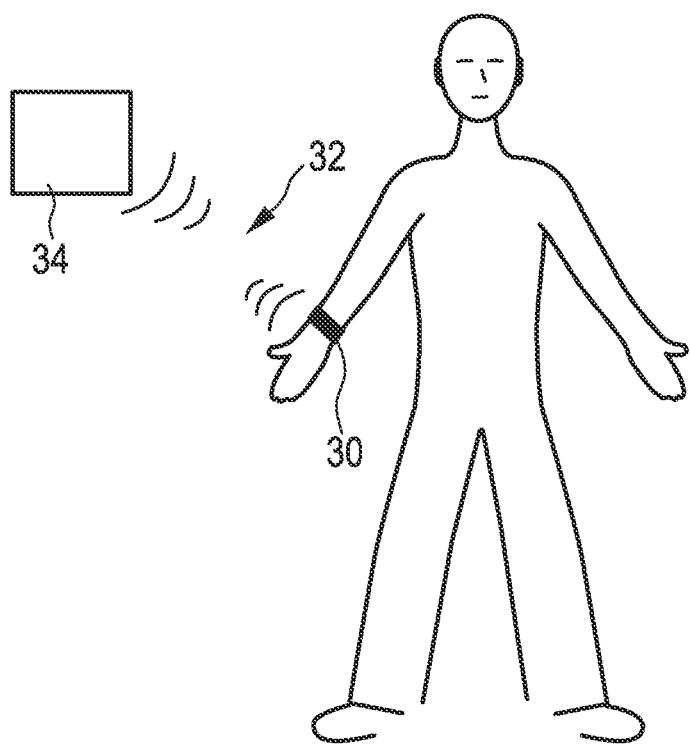
FIG. 6 shows an illustration of an emotional event detection system according to an embodiment of the present invention.

FIG. 6 shows an illustration of an emotional event detection system according to an embodiment. The emotional event detection system detects an emotional event of a user. The system comprises a skin conductance sensor 20, which is integrated into the wristband 30 shown in FIG. 6. The wristband 30 shown in FIG. 6 can for example be the wristband 30 of the embodiment in FIG. 5. The system further comprises a processing unit 34 adapted to process the transmitted data and detect an emotional event in the user based on the transmitted data. The processing unit 34 can be a separate part. The system also comprises a transmission link 32, between the skin conductance sensor 20 and the processing unit 34, for transmitting data indicative of the sensed skin conductance, for example the measured skin conductance values. The transmitter in the wristband 30, such as transmitter 28 in FIG. 5 or FIG. 4, transmits data indicative of the sensed skin conductance to a receiver of the processing unit 34 over the wireless transmission link 32. The transmission link 32 illustrated in FIG. 6 is a wireless link. However, also other transmission links are possible, such as transmission by downloading data from a memory or using a cable. Even though not illustrated in FIG. 6, the system can comprise at least one further sensor, such as a heart rate sensor, for example for measuring heart rate variations, a breathing sensor, a blood sensor, a body temperature sensor, a voice sensor, a camera for capturing the face of the user, or the like. Each of these further sensors can be adapted to transmit the sensed data to the processing unit 34. The processing unit 34 can then combine the measurements from the skin conductance sensor with measurements of other sensors, in order to improve the accuracy of the emotional event detection.

Figure 7:
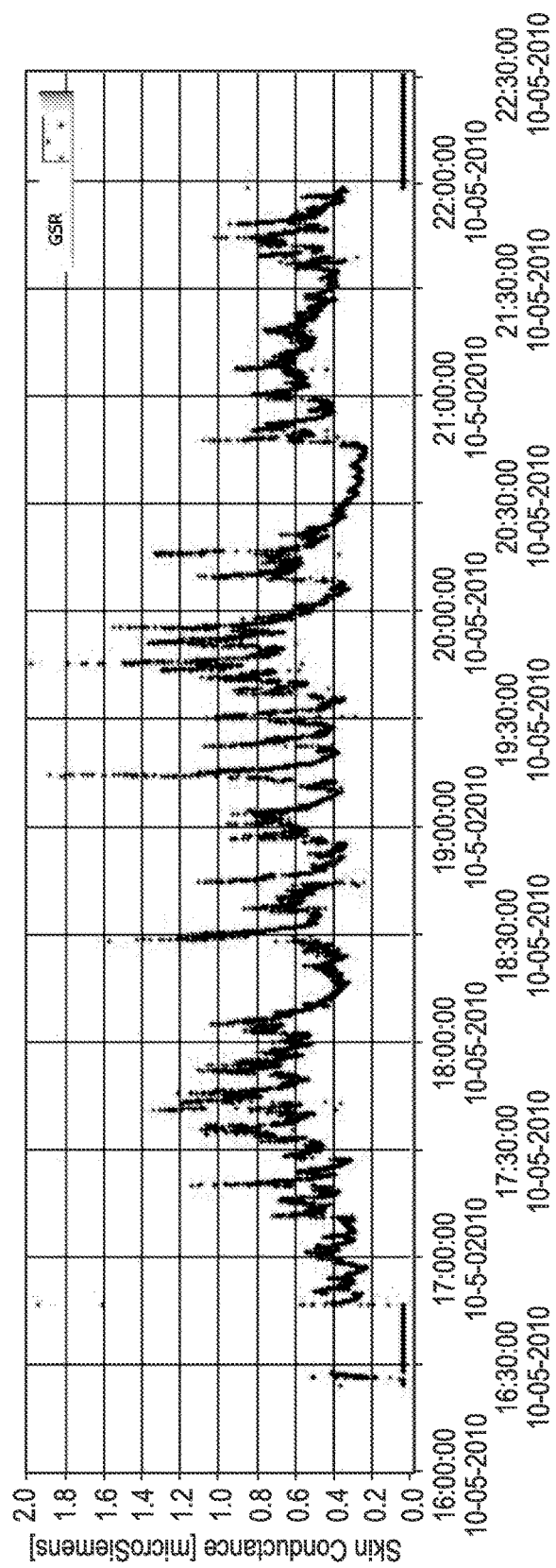
FIG. 7 shows a skin conductance trace, sensed by a skin conductance sensor according to an embodiment of the present invention, for determining emotional events.

FIG. 7 shows a skin conductance trace sensed by a skin conductance sensor according to an embodiment, in particular measured with the skin conductance sensor or wristband as previously described. The skin conductance trace shows several hours of measurement. The processing unit 34 shown in FIG. 6 is adapted to detect a particular rising slope and/or a particular down slope in the transmitted skin conductance data, in particular detecting peaks with a steeper rising slope and more gentle down slope. In this way, an emotional event can be detected. Skin conductance is related with the level of arousal of the user. Everything that emotionally touches the user activates the sweat glands in the skin leading to a better conductor path through the skin. Hence, an easy way of determining emotional events from skin conductance data is provided.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method of providing a skin conductance sensor, the skin conductance sensor comprising first and second dry electrodes, the sensor being adapted to sense skin conductance of skin of a user between the first and second dry electrodes, the first and second dry electrodes being dry skin conductance electrodes for contacting the skin of the user, the method comprising:
   providing, for the first and second dry electrodes, at least one inner layer, the inner layer comprising metal; and
   providing, for the first and second dry electrodes, an outer layer, the outer layer comprising a material made of a noble metal doped with at least one dopant selected from the group consisting of hydrogen, lithium, sodium, potassium, rubidium, cesium and beryllium, wherein the noble metal comprises one or more of ruthenium, rhodium, palladium, osmium, iridium, platinum, or gold, wherein the outer layer is disposed at an outer surface of the first and second dry electrodes for interfacing with the skin such that the first and second dry electrodes and the skin form a non-polarizable skin-electrode interface, and wherein the outer layer is provided via one of the following: (i) sputtering or (ii) co-deposition in vacuum by evaporation and/or e-beam deposition or co-deposition in vacuum.

2. The method of claim 1, wherein the noble metal of the outer later is e-beam deposited and the at least one dopant is deposited in vacuum by evaporation.

3. The method of claim 1, wherein providing the outer layer further comprises monitoring the thickness of the outer layer.

4. The method of claim 3, where monitoring the thickness comprises monitoring the thickness to be less than 1 micron.

5. The method of claim 1, wherein the noble metal comprises gold and the dopant comprises lithium.

6. The method of claim 1, further comprising cleaning a surface of the at least one inner layer facing the outer layer via reactive ion etching prior to providing the outer layer.

7. The method of claim 1, wherein the at least one inner layer comprises a first inner layer and a second inner layer.

8. The method of claim 7, wherein the first and second inner layer comprise at least one of: nickel and brass.

9. The method of claim 8, wherein the second inner layer is in the form of a plate.

10. The method of claim 9, wherein the second inner layer is a plate polished and electrochemically plated with the first inner layer.

11. The method of claim 1, wherein the noble metal comprises gold and the dopant comprises lithium, wherein the noble metal is e-beam deposited, and wherein the dopant is deposited in vacuum via evaporation from a heated crucible.

12. The method of claim 1, wherein the outer layer comprises gold doped with lithium, wherein the outer layer is provided via sputtering.

* * * * *